United States Patent [19]

Lee et al.

[11] Patent Number: 4,745,189
[45] Date of Patent: May 17, 1988

[54] METHOD OF PREPARING N-HALOGENATED ORGANIC HETEROCYCLIC COMPOUNDS

[75] Inventors: John Y. Lee; Mark A. Templeton, both of Baton Rouge, La.

[73] Assignee: Ethyl Corporation, Richmond, Va.

[21] Appl. No.: 877,154

[22] Filed: Jun. 23, 1986

[51] Int. Cl.$^4$ .................. C07D 251/00; C07D 239/02
[52] U.S. Cl. .................................... 544/221; 548/311; 548/545
[58] Field of Search ................ 548/311, 545; 544/221; 514/389, 425, 241

[56] References Cited

U.S. PATENT DOCUMENTS

| | | | |
|---|---|---|---|
| 2,130,805 | 9/1938 | Levine | 548/311 |
| 2,398,598 | 4/1946 | Rogers | 548/311 |
| 3,147,259 | 9/1964 | Paterson | 548/545 |
| 3,345,371 | 10/1967 | Paterson | 548/545 |
| 3,412,021 | 11/1968 | Paterson | 548/311 |

FOREIGN PATENT DOCUMENTS 2503049 10/1978 Fed. Rep. of Germany ...... 548/545

Primary Examiner—Henry R. Jiles
Assistant Examiner—Robert C. Whittenbaugh
Attorney, Agent, or Firm—Donald L. Johnson; John F. Sieberth; W. G. Montgomery

[57] ABSTRACT

A method of preparing N-halogenated organic heterocyclic compounds by reacting in an aqueous mixture under alkaline conditions (e.g. NaOH) and in the presence of a halogenated organic compound (e.g. methylene chloride), a N-hydrogen organic heterocyclic compound containing at least one NH group (e.g. 5,5-dimethylhydantoin) and a halogen-producing chemical (e.g. $Br_2$).

19 Claims, No Drawings

METHOD OF PREPARING N-HALOGENATED ORGANIC HETEROCYCLIC COMPOUNDS

BACKGROUND OF THE INVENTION

A. Field of the Invention

This invention relates to the preparation of N-halogenated organic heterocyclic compounds which have particular application in treating water, such as disinfecting or controlling the biofouling of the water.

B. Description of the Prior Art

Halogens, especially chlorine and bromine, have long been used for water treatment since they exhibit a broad spectrum of bactericidal activity at low concentrations. Of the two, chlorine has a wider application, being supplied as a pure gas in pressurized cylinders, or alternatively, as a liquid or solid hypochlorite containing 5 to 70% by weight available chlorine. Dosage of these concentrated forms of chlorine is so small that finely calibrated metering devices are required for field use. Furthermore, chlorine residuals in water must be maintained within close tolerances, since concentrations only slightly higher than the effective minimum are often irritating to the eyes, nose and skin. To maintain chlorine residuals within close tolerances requires careful metering of the chlorine and precise performance of the sensitive gas injectors or liquid metering pumps. Since these mechanical devices are continuously exposed and subjected to a highly corrosive environment, malfunction of the devices is common. This can result in dangerously high concentrations of chlorine in the water or, conversely, chlorine residuals can become so low as to be bactericidally ineffective.

Another factor which makes the maintenance of satisfactory chlorine residuals difficult with conventional metering equipment is the varying chlorine demand of the water, particularly as exemplified by the continuously changing requirements for chlorine in a swimming pool. For instance, during heavy use, the chlorine residual requirements will increase greatly for water disinfection. To properly compensate for such variable chlorine requirements involves frequent manual resetting of the metering device. Attempts have been made to correct this shortcoming by providing sensors in the treated water with feedback controls to the chlorine feeder to continuously readjust the pumping rate. Such systems are expensive and can themselves malfunction.

Bromine is an excellent water disinfectant but has very limited use in the present art because liquid bromine causes severe burns if allowed to contact the skin, and its fuming vapors are highly corrosive and toxic. Inorganic hypobromites have not been successfully offered in commerce since they are extremely unstable, reverting in a short period of time to germicidally inactive bromate.

In an effort to overcome the foregoing problems, N-halogenated organic compounds such as N-brominated-N-chlorinated organic compounds have been developed for water treatment. An advantage of these compounds is that they are solids which makes them relatively safe to handle. In addition, they may contain high percentages of bromine, as well as chlorine, which affords the further advantage of being able to maintain good halogen residuals in water.

When N-halogenated organic heterocyclic compounds, such as N-bromo-N'-chloro-5,5-dimethylhydantoin are utilized for water treatment, it is necessary that they have sufficient particle size. The reason for this requirement is that the compounds must exhibit good solubility in water but have a relatively low solubility when they have sufficient particle size, such as in the form of a cohesive solid mass. Low solubility of the compounds having sufficient particle size allows them to be immersed in the water for long periods of time without substantial loss of potency.

In addition, it is desirable that N-halogenated organic heterocyclic compounds have sufficient particle size because of the very dusty and corrosive nature of the compounds. Airborne particles of the N-halogenated organic heterocyclic compounds can cause an unsatisfactory work environment and high maintenance costs in equipment coming into contact with the compounds.

When the N-halogenated heterocyclic organic compound particles have sufficient size, dissolution of the particles is restricted to the outer surface of the particle which allows them to be immersed in water for long periods of time without a substantial loss of potency. In addition, restricting the dissolution ratio of the particles allows a controlled addition of the halogens to the water. This allows the N-halogenated organic heterocyclic compounds to perform as a chemical sensor which is capable of an autonomic response. Because of this property, the dissolution rate of the particles in water increases in response to the contamination load in the water.

Methods of preparing N-halogenated organic heterocyclic compounds are known. For instance, U.S. Pat. No. 3,147,259 discloses the preparation in an aqueous alkaline medium of such compounds by treating an N-hydrogen organic heterocyclic compound, having at least two N-hydrogen radicals, with chlorine in the presence of a bromine-producing chemical. German Pat. No. 2,503,049 discloses the preparation of N-bromo-N-chloro-5,5-dimethylhydantoin by reacting 5,5-dimethylhydantoin in an aqueous alkali carbonate solution containing a wettiing agent at a temperature of 0° to 15° C. U.S. Pat. No. 3,345,371 discloses the preparation of N-brominated-N-chlorinated organic heterocyclic compounds by mixing a multi-N-brominated organic heterocyclic compound with a multi-N-chlorinated organic heterocyclic compound. U.S. Pat. No. 3,412,021 discloses the preparation of particles of N-halogenated organic heterocyclic compounds in the form of a cohesive mass by utilizing a binder and compressing the particles into a compacted mass, such as by tableting or briquetting.

A problem associated with compressing particles of N-halogenated organic heterocyclic compounds into a compacted mass to obtain proper size is the added expenses of the equipment necessary for compressing the particles and the additional necessity of first preparing the N-halogenated compounds prior to compressing them into a cohesive mass. Since the N-halogenated organic heterocyclic compounds are corrosive, this results in high maintenance cost of the equipment used therein and associated dusting problems.

The present invention provides a method of preparing N-halogenated organic heterocyclic compounds which overcomes or at least mitigates the above described problems.

SUMMARY OF THE INVENTION

The present invention relates to a method of preparing N-halogenated organic heterocyclic compounds which have sufficient particle size that they can be immersed in water for long periods of time without a substantial loss of potency. In addition, the increased size of particles results in a more satisfactory work environment and a lower cost of equipment used in the preparation of the N-halogenated organic heterocompounds. This particle size enlargement occurs without the need of additional processing steps such as compacting of the N-halogenated organic heterocyclic compounds.

The N-halogenated organic heterocyclic compounds of the invention have particular application in disinfecting water in aqueous systems such as swimming pools, spas, industrial waste water systems, and similar type environments and controlling biofouling in recirculating water systems. Treatment of such systems is carried out by contacting the water contained therein with a biocidally effective amount of the compounds. Generally, from 1 to 2 ppm or greater active halogen in the system is sufficient to disinfect and maintain the system.

DETAILED DESCRIPTION OF THE INVENTION

The N-halogenated organic heterocyclic compounds to which this invention pertains are those which contain at least one N-halo radical such as chloro, bromo or iodo radicals. In addition, N,N'-dihalo organic compounds or mixed N,N'-dihalo organic heterocyclic compounds which contain more than a single halo radical in the carrier molecule, such as for example N,N'-bromochloro-5,5-dimethylhydantoin, may be prepared.

Generally the N-halogenated organic heterocyclic compounds of the present invention may be classified as N-halogenated organic heterocyclic compounds having the following typical formulae:

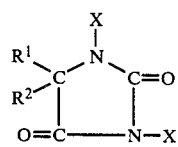
I

In the above formula I, $R^1$ and $R^2$ are independently selected from the group consisting of hydrogen, aryl, alkylaryl, arylalkyl, a lower alkyl having 1 to 6 carbon atoms, a cycloalkyl having 3 to 7 carbon atoms, and $R^1$ and $R^2$ together can form a cycloalkyl having 3 to 7 carbon atoms and X is selected from the group consisting of hydrogen or a halogen such as bromine, chlorine, iodine and mixtures thereof provided however that at least one X is a halogen;

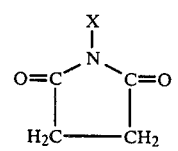
II

In the above formula II, X is a halogen such as iodine, chlorine and bromine; and

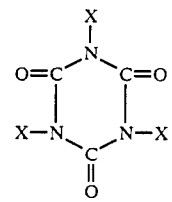
III

In the above formula III, X is hydrogen or a halogen such as chlorine, bromine and iodine provided however that at least one X is a halogen.

Examples of compounds corresponding to formula I can generally be described as N-halogenated hydantoins and include N,N'-dichloro-5,5-dimethylhydantoin, N,N'-bromochloro-5,5-dimethylhydantoin, N',N-dibromo-5,5-dimethylhydantoin, 1-chloro-5,5-dimethylhydantoin, 3-chloro-5,5-dimethylhydantoin, 1-bromo-5,5-dimethylhydantoin, 3-bromo-5,5-dimethylhydantoin, N,N'-dichloro-5-ethyl-5-methylhydantoin, N,N'-dibromo-5-ethyl-5-methylhydantoin, N,N'-bromochloro-5-ethyl-5-methylhydantoin, N,N'-bromochloro-5-ethyl-5-phenylhydantoin, N,N'-dibromo-5-methyl-5-phenylhydantoin, N,N'-bromochloro-5-methyl hydantoin, N,N'-dichloro-5-methylhexylhydantoin, N,N'-dichloro-5,5-di(p-methylphenyl)hydantoin, and N,N'-bromochloro-5,5-dibenzylhydantoin.

Examples of compounds corresponding to formula II which can generally be described as N-halogenated succinimides include N-bromo succinimide, N-chloro succinimide and N-iodo succinimide.

Examples of compounds corresponding to formula III can generally be described as N-halogenated cyanurates and include 1,3,5-trichlorocyanurates, 1,3,5-tribromocyanurates, 1,3,5-triiodocyanurates, and mixed trihalocyanurates.

In one embodiment of the method of the present invention, the N-halogenated organic heterocyclic compound can be prepared by reacting in an aqueous mixture under alkaline conditions a N-hydrogen organic heterocyclic compound containing at least one divalent organic moiety selected from the group consisting of:

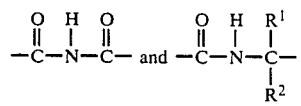

wherein $R^1$ and $R^2$ are independently selected from the group consisting of hydrogen, an alkyl having from 1 to about 6 carbon atoms, aryl, arylalkyl, alkylaryl, and a cycloalkyl having 3 to 7 carbon atoms and provided further that $R^1$ and $R^2$ together can form a cycloalkyl having 3 to 7 carbon atoms; and a halogen-producing compound, such as bromine, in the presence of a halogenated organic compound.

The halogenated organic compounds which are suitable for use in the method of the invention include halogenated aliphatic compounds having 1 to about 6 carbon atoms, halogenated aromatic compounds, and halogenated alicyclic compounds having about 6 carbon atoms.

The invention also relates to processes for preparing mixed dihalo compounds including N-bromo-N'-chloro organic heterocyclic compounds such as N-bromo-N'- chloro-5-substituted hydantoins. By modification of the method applicable to preparing N-halo organic heterocyclic compounds, it is possible to prepare the mixed dihalo materials. For instance, in the case of a 5-substituted hydantoin, the method can be carried out by treating one mole of the 5-substituted hydantoin in an aqueous mixture under alkaline conditions and in the presence of a halogenated organic compound with an amount of bromine-producing compound of one-half mole of bromine or one mole of bromide salt and chlorinating the resulting mixture to produce the desired N-bromo-N'-chloro-5-substituted hydantoin.

Under these conditions, the initial one-half mole of bromine will introduce one bromine in one-half of the hydantoin and will also form one-half mole of NaBr. Upon chlorination, the chlorine will liberate the bromine from NaBr which will then substitute a bromine in the remaining one-half mole of the hydantoin. The rest of the chlorine, at least one mole, will chlorinate the remaining N—H groups in the hydantoin. The final product is N-bromo-N'-chloro-5-substituted hydantoin. Although the reaction has been described in a stepwise fashion, no sequence is required as chlorine and bromine may be introduced into the aqueous alkaline mixture or concurrently containing the 5-substituted hydantoin in any sequence.

The following equation is representative of one embodiment the process of preparing the mixed dihalo compounds:

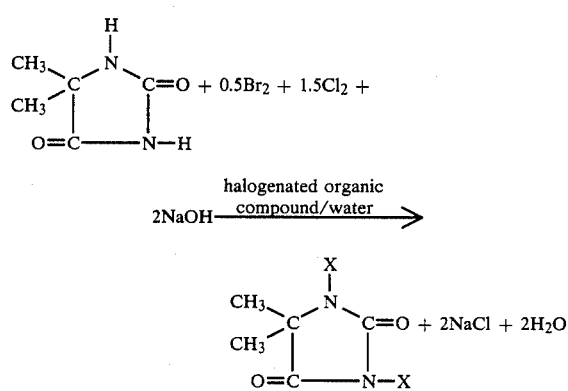

wherein one X is Br and the other is Cl.

While the foregoing process has been specifically directed to preparing mixed dihalo 5-substituted hydantoins, the process is applicable to other N-hydrogen heterocyclic compounds which contain 1 to 3 N-H radicals adjacent to a carbonyl group. For instance, cyanuric acids contain three replaceable hydrogens in the N-H radicals. Treatment of a mole of cyuranic acid with less than 1.5 moles of bromine and chlorination with chlorine, will produce a mixture of cyanuric acids having both N-chloro and N-bromo substituents. In like manner, a mole of cyanuric acid treated with two moles of NaBr and chlorinated will result in N,N''-dibromo-N'-chloro cyanuric acid. The chlorine will react with NaBr to form NaCl and $Br_2$ or BrCl which will brominate two of the nitrogen atoms. The remaining nitrogen atoms will be chlorinated. Alternatively, two moles of bromine could be reacted initially followed by chlorination.

The present invention also contemplates the production of N-halogen carriers wherein all of the N-hydrogens are not substituted with halogen atoms. Thus it is possible to produce an admixture of N-bromo-N'-bromo-5-substituted hydantoin with N-mono-bromo-5-substituted hydantoin. One method of accomplishing this involves using less than the theoretical amount of the alkali material and terminating bromination when the reaction mixture reaches an acidic pH.

The N-hydrogen organic heterocyclic compounds which are suitable as starting materials include N-hydrogen organic heterocyclic compounds which contain at least one divalent organic moiety selected from the group consisting of:

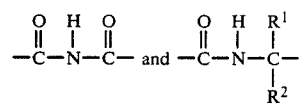

wherein $R^1$ and $R^2$ are independently selected from the group consisting of hydrogen, an alkyl having 1 to about 6 carbon atoms, such as methyl, ethyl, n-propyl, 2-propyl, cyclo-propyl, n-butyl, 2-butyl, iso-butyl, t-butyl, and cyclobutyl, aryl, arylalkyl, alkylaryl, and a cycloalkyl having 3 to about 7 carbon atoms and provided further that $R^1$ and $R^2$ together can form a cycloalkyl having 3 to about 7 carbon atoms.

Examples of suitable starting compounds include:

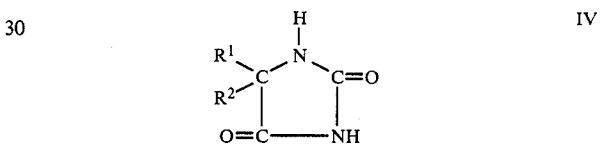

In above formula IV, $R^1$ and $R^2$ are independently hydrogen, a lower alkyl having 1 to about 6 carbon atoms, aryl, arylalkyl, alkylaryl, a cycloalkyl having about 3 to about 7 carbon atoms and provided further that $R^1$ and $R^2$ together can form a cycloalkyl having 3 to about 7 carbon atoms.

Examples of compounds corresponding to formula IV include:

5,5-dimethylhydantoin;
5-methyl-5-n-amylhydantoin;
5-methyl-5-n-butylhydantoin;
5-methyl-5-isobutylhydantoin;
5-methyl-5-phenylhydantoin;
5-ethyl-5-phenylhydantoin;
5-methyl-5-cyclohexylhydantoin;
5-pentamethylene-5-spirohydantoin;
5-ethyl-5-phenylhydantoin;
5-methyl-5-phenylhydantoin;
5-methylhydantoin;
5-methyl-hexylhydantoin;
di(p-methylphenyl)hydantoin; and
5,5-dibenzylhydantoin.

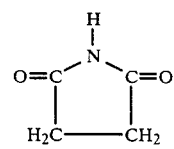

Formula V represents succinimide.

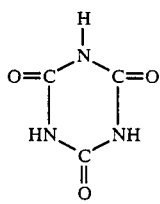

Formula VI represents cyanuric acid.

The alkaline conditions described above may be provided by ordinary bases such as alkali metal hydroxides such as potassium hydroxide, sodium hydroxide and lithium hydroxide, sodium bicarbonate, sodium carbonate, magnesium oxide, magensium carbonate, magnesium hydroxide, calcium oxide, calcium hydroxide, barium hydroxide, and calcium carbonate and mixtures thereof. Preferably, the basic material is sodium hydroxide. Preferably, the amount of alkaline material used in the method of the invention is an amount sufficient to neutralize any by-product hydrogen halides formed during the reaction. In the case of preparing a 5-substituted-1,3-dihalogenated hydantoin, preferably two equivalents of alkaline material are used per mole of the hydantoin.

The halogen-producing compound may be any halogen such as elementary bromine, chlorine or iodine or a bromide or iodide salt, for example, a bromide or iodide salt of an alkali metal (sodium, potassium or lithium) or an alkaline earth metal (calcium or magnesium).

The amount of halogen-producing compound utilized in the method of the invention is preferably at least one equivalent of the halide producing compound for each replacement of a removable hydrogen contained in the N—H radicals. Thus, where the starting material contains a single N—H group, such as with a succinimide, an equivalent of halogen-producing material preferably corresponds to one (1) gram atom. In the instance of elemental bromine, 160 grams or one mole should be used per mole of starting material. Alternatively, one-half mole of bromine can be used to introduce one-half of the required bromine and the bromination can then be completed by adding at least one-half mole of chlorine to oxidize by-product back to bromine. Similarly, where a bromide, such as NaBr is used, one mole of such bromide in combination with at least one mole of chlorine should be used. When the starting material contains two N—H radicals, two equivalents of the bromine-producing material would be two moles of bromine (Br$_2$) or two moles of bromide salt such as NaBr in combination with two moles of chlorine per mole of starting material to produce a N,N-dibromo compound.

The advantageous effect of the halogenated organic compounds in the course of the halogenation of the N-hydrogen organic heterocyclic compound is the suppression of foam, an increase in the reactor loading capacity, and an increase in particle size of the N-halogenated organic heterocyclic compound produced during the reaction and ease of preparing large tablets of the halogenated organic compounds, i.e., 3 inch by ½ inch tablets. For example, in the preparation of N,N'-bromo-chloro5,5-dimethyl hydantoin, a particle size of the hydantoin of from about 1/16 to about ⅛ inch can be achieved.

Although the invention is not intended to be limited to any particular theory of operation, it is believed that the halogenated organic compounds adsorb on the N-halogenated organic heterocyclic compound particles in the aqueous mixture and form liquid bridges between the particles by coalesence during the collisions that occur during the reaction. This results in particle size increases in the N-halogenated organic heterocyclic compounds.

Generally, the halogenated organic compounds useful in the process of the present invention must be generally immiscible in the aqueous alkaline composition. Suitable halogenated organic compounds include halogenated aliphatic compounds having from 1 to about 6 carbon atoms, halogenated aromatic compounds and halogenated alicyclic compounds having about 6 carbon atoms.

Examples of such compounds include monohalomethanes, such as monoiodomethane, dihalomethanes, such as dibromomethane, dichloromethane, diiodomethane, chlorobromomethane, halobutanes such as chlorobutane, bromobutane, iodobutane, 1,1-dichloroethane, 1,2-dichloroethane, 1,1,1-trichloroethane, sym-tetrachloroethane, and the like, halogenated cyclohexanes such as 1-bromocyclohexane and 1-chlorocyclohexane and halogenated aromatic compounds such as chlorobenzene and bromobenzene. The preferred compound is dichloromethane.

The amount of organic halogenated compound used in the method of the invention will be an amount in the range of from about 5 to 95 weight percent of combined weight of water and organic halogenated compound used in the aqueous mixture. Preferably, the organic halogenated compound is present in an amount of from about 10 to 50 percent and more preferably is present in an amount of 35 percent of the combined weight of water and organic halogenated compound used in the aqueous mixture.

In carrying out the method of the invention, it is preferred that the amount of N-hydrogen organic heterocyclic compound utilized be an amount which allows the N-hydrogen organic heterocyclic componds to be slurried in the aqueous mixture. Thus, it is preferred that the N-hydrogen organic heterocyclic compounds be present in the aqueous mixture in an amount of from about 5 to about 30 percent by weight of water and organic halogenated compound used and, more preferably, from about 6 to 10 percent by weight of water and organic halogenated compound used.

The reaction is preferably carried out at a temperature of from about 0° C. to about 60° C. More preferably the temperature is from about 0° to about 35° C. and, most preferably, from about 0° C. to about 15° C.

The present invention is further exemplified by the examples below which are presented to illustrate certain specific embodiments of the invention, but are not intended to be construed so as to be restrictive of the spirit and scope thereof.

EXAMPLE I

To a 500 ml, three-neck flask equipped with an agitator, cooling means, a thermometer, and bromine and chlorine subsurface feed means were charged 10 grams (0.25 mole) of sodium hydroxide, 200 grams of water, 16 grams (0.125 mole) of 5,5-dimethylhydantoin (DMH), and 13.2 grams of dichloromethane under agitation at 15° C. Then, 15 grams (0.0625 mole) of bromine was fed into the reactor over a period of 2 minutes. Next 13.4 grams (0.188 mole) of chlorine was fed into the reactor over a period of 12 minutes and a pH of 5.5 was achieved. A temperature of 15° C. was maintained during the reaction. The resulting product, N-bromo-N'-chloro-5,5-dimethylhydantoin (BCDMH), which comprised particles having a diameter from about 1/16 (inch) to about ⅛ inch, was filtered using a Buchner funnel and washed with 20 ml of water. The BCDMH was dried at 60° C. under reduced pressure for four hours. The yield of BCDMH was 26.8 grams which was 89% of theoretical.

EXAMPLE II

A procedure and stoichiometry identical to Example I was utilized for the Example except that 26.4 grams rather than 13.2 grams of dichloromethane was used. The resulting product BCDMH comprised particles having a diameter from 1/10 (inch) to 1/6 inch. The yield of BCDMH was 84% of theoretical.

EXAMPLE III

A procedure and stoichiometry identical to Example I was utilized except that 264 grams instead of 13.2 grams of dichloromethane and 20 grams instead of 200 grams of water, were used. The resulting product BCDMH comprised particles having a diameter of 1/16 (inch) to ⅛ inch. The yield of BCDMH was about 90% of theoretical.

EXAMPLE IV

To a 12 liter reactor equipped with an agitator, cooling means and bromine and chlorine subsurface feed means, were charged 4800 grams of tap water, 729 grams of sodium hydroxide, 1152 grams of 5,5-dimethylhydantoin (DMH) and 450 grams of dichloromethane under agitation. Then 647 grams of bromine was fed subsurfacely into the reaction mixture over a period of about 20 minutes. Next 850 grams of chlorine was fed subsurfacely into the reactor over a period of 3 hours. A temperature of 15° C. was maintained during the reaction. The resulting product, N-bromo-N'-chloro-5,5-dimethylhydantoin (BCDMH), which comprised particles having a diameter from 1/16 inch to 150 inch, was filtered using a Buchner funnel and washed with 1 quart of water. The BCDMH was dried in a fluidized bed dryer. The yield of BCDMH was 1882 grams.

The invention is not limited to the above-described specific embodiments thereof; it must be understood therefore, that the details involved in the descriptions of these embodiments is presented for the purposes of illustration only, and that reasonable variations and modifications which will be apparent to those skilled in the art can be made of this invention without departing from the spirit and scope thereof.

We claim:

1. In a method of preparing a N-halogenated organic heterocyclic compound comprising reacting in an aqeuous mixture under alkaline conditions:
   (a) a N-hydrogen organic heterocyclic compound containing at least one divalent organic moiety selected from the group consisting of

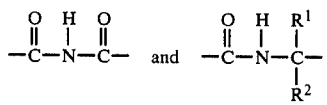

wherein $R^1$ and $R^2$ are independently selected from the group consisting of hydrogen and an alkyl having 1 to about 6 carbon atoms, aryl, arylaklyl, alkylaryl, and a cycloalkyl having about 3 to about 7 carbon atoms and provided further that $R^1$ and $R^2$ together can form a cycloalkyl having about 3 to about 7 carbon atoms; and,
   (b) a halogen-producing chemical;
the improvement comprising conducting said reaction in the the presence of a halogenated organic compound selected from the group consisting of halogenated aliphatic compounds having from 1 to about 6 carbon atoms, halogenated aromatic compounds and halogenated alicyclic compounds having about 6 carbon atoms wherein said halogenated organic compound is present in said aqeuous mixture in an amount in the range of from about 5 to about 95 weight percent of the combined weight of the water and said halogenated organic compound to increase the particle size of said N-halogenated organic heterocyclic compound.

2. The method recited in claim 1 wherein said N-hydrogen organic heterocyclic compound is selected from the group consisting of:

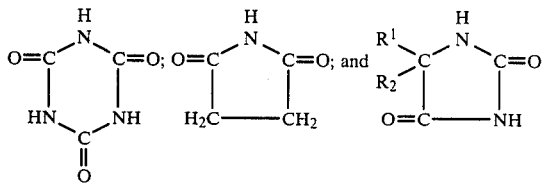

wherein $R^1$ and $R^2$ are independently selected from the group consisting of hydrogen, a lower alkyl having 1 to about 6 carbon atoms, aryl, arylalkyl, alkylaryl, a cycloalkyl having about 3 to about 7 carbon atoms, a cycloalkyl formed from $R^1$ and $R^2$ together having about 3 to about 7 carbon atoms.

3. The method recited in claim 2 wherein said N-halogenated organic heterocyclic compound has the following formula:

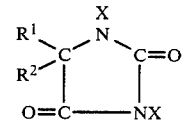

wherein X is selected from the group consisting of hydrogen, bromine, chlorine, iodine and mixtures thereof and provided further that at least one X is bromine, chlorine or iodine and $R^1$ and $R^2$ are selected from the group consisting of hydrogen and an alkyl having 1 to about 6 carbon atoms.

4. The method recited in claim 3 wherein said alkaline conditions are provided by a base selected from the group consisting of sodium hydroxide, potassium hydroxide, lithium hydroxide, sodium bicarbonate, sodium carbonate, calcium oxide, calcium hydroxide, magnesium oxide, magnesium carbonate, magensium hydroxide, barium hydroxide, calcium carbonate, and mixtures thereof.

5. The method recited in claim 4 wherein said base is present in an amount sufficient to neutralize by-product hydrogen halide formed during the preparation of said N-halogenated organic heterocyclic compound.

6. The method recited in claim 5 wherein the reaction is carried out at a temperature in the range of from about 0° to about 35° C.

7. The method recited in claim 4 wherein said halogenated organic compound is selected from the group consisting of monoiodomethane, dibromomethane, dichloromethane, diiodomethane, chlorobromomethane, chlorobutane, bromobutane, iodobutane, 1,1-dichloroethane, 1,2-dichloroethane, 1,1,1-trichloroethane, sym-tetrachloroethane, 1-bromocyclohexane, 1-chlorocyclohexane, chlorobenzene, bromobenzene, and mixtures thereof.

8. The method recited in claim 7 wherein said halogenated organic compound is present in said aqueous mixture in an amount in the range of from about 10 to about 50 weight percent of the combined weight of the water and said halogenated organic compound.

9. The method recited in claim 8 wherein said halogen-producing chemical is bromine or chlorine, and combinations thereof and said halogenated organic compound is dichloromethane.

10. In a method of preparing an N-bromo-N'-chloro organic heterocyclic compound comprising reacting in an aqueous mixture under alkaline conditions:
(a) a N-hydrogen organic heterocyclic compound having at least two N-hydrogen moieties and selected from the group consisting of:

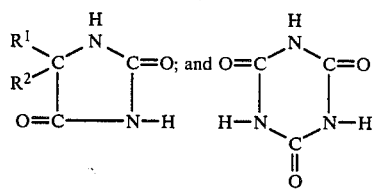

wherein $R^1$ and $R^2$ are independently selected from the group consisting of hydrogen, aryl, arylalkyl, alkylaryl, lower alkyl having 1 to about 6 carbon atoms, and cycloalkyl having about 3 to about 7 carbon atoms, and cycloalkyl formed from $R^1$ and $R^2$ together having 3 to about 7 carbon atoms;
(b) with chlorine and a bromine-producing compound selected from the group consisting of elemental bromine, alkali metal bromides, alkaline earth metal bromides and mixtures thereof said bromine-producing compound being present in an amount sufficient to produce at least one N-bromo radical but less that sufficient to brominate all N-hydrogen radicals and said chlorine being present in an amount sufficient to produce at least one N-chloro radical;
the improvement comprising conducting said reaction in the presence of a halogenated organic compound selected from the group consisting of halogenated aliphatic compounds having from 1 to about 6 carbon atoms, halogenated aromatic compounds and halogenated alicyclic compounds having about 6 carbon atoms wherein said halogenated organic compound is present in said aqueous mixture in an amount in the range of from about 5 to about 95 percent of the combined weight of the water and said organic halogenated compound to increase the particle size of said N-bromo-N'-chloro organic heterocyclic compound.

11. The method of claim 10 wherein said N-hydrogen organic heterocyclic compound is selected from the group consisting of 5,5-dimethylhydantoin, 5-methyl-5-n-amylhydantoin, 5-methyl-5-n-butylhydantoin, 5-metyl-5-isobutylhydantoin, 5-methyl-5-phenylhydantoin, 5-ethyl-5-phenyhydantoin, 5-methyl-5-cyclohexylhydantoin, 5-pentamethylene-5-spirohydantoin and mixtures thereof.

12. The method recited in claim 11 wherein said alkaline conditions are provided by a base selected from the group consisting of sodium hydroxide, potassium hydroxide, lithium hydroxide, sodium biocarbonate, sodium carbonate, calcium oxide, calcium hydroxide, magnesium oxide, magnesium carbonate, magnesium hydroxide, barium hydroxide, calcium carbonate, and mixtures thereof.

13. The method recited in claim 12 wherein said base is present in an amount sufficient to neutralize by-product hydrogen halide formed during the preparation of said N-bromo-N'-chloro organic heterocyclic compound.

14. The method recited in claim 12 wherein said bromine-producing compound is sodium bromide in combination with chlorine.

15. The method recited in claim 12 wherein said halogenated organic compound is selected from the group consisting of monoiodomethane, dibromomethane, dichloromethane, diiodomethane, chlorobromomethane, chlorobutane, bromobutane, iodobutane, 1,1-dichloroethane, 1,2-dichloroethane, 1,1,1-trichloroethane, sym-tetrachloroethane, 1-bromocyclohexane, 1-chlorocyclohexane, chlorobenzene, bromobenzene, and mixtures thereof.

16. The method recited in claim 15 wherein said halogenated organic compound is present in said aqueous mixture in an amount in the range of from about 10 to about 50 weight percent of the combined weight of the water and halogenated organic compound.

17. The method recited in claim 16 wherein said halogenated organic compound is dichloromethane.

18. The method recited in claim 17 wherein the reaction is carried out at a temperature in the range of from about 0° to about 35° C.

19. In a method of preparing N-bromo-N'-chloro-5,5-dimethylhydantoin comprising:
reacting 5,5-dimethylhydantoin in an aqueous mixture under alkaline conditions provided by sodium hydroxide with bromine in an amount sufficient to produce at least one N-bromo group but less than sufficient to brominate both N-hydrogen groups and chlorine in an amount sufficient to produce at least one N-chloro group;
the improvement comprising conducting said reaction in the presence of dichloromethane wherein said dichloromethane is present in the aqueous mixture in an amount in the range of from about 5 to about 95 of the combined weight of the water and said dichloromethane to increase the particle size of said N-bromo-N'-5,5-dimethylhydantoin.

* * * * *

UNITED STATES PATENT AND TRADEMARK OFFICE
CERTIFICATE OF CORRECTION

PATENT NO.  : 4,745,189

DATED       : May 17, 1988

INVENTOR(S) : John Y. Lee, et al.

It is certified that error appears in the above-identified patent and that said Letters Patent is hereby corrected as shown below:

Column 4, line 26, reads "-5-methyl hydantoin," and should read -- -5-methylhydantoin, --.

Column 7, line 63, reads "-chloro5,5-" and should read -- -chloro-5,5- --.

Column 7, line 63, reads "5,5-dimethyl hydantoin" and should read -- 5,5-dimethylhydantoin --.

Column 9, line 41, reads "to 150 inch" and should read -- to 1/8 inch --.

Column 9, line 55, reads "in an aqeuous" and should read -- in an aqueous --.

Column 11, line 48, reads "less that sufficient" and should read -- less than sufficient --.

Column 12, line 8, reads "5-ethyl-5-phenyhydantoin" and should read -- 5-ethyl-5-phenylhydantoin --.

Column 12, line 60, reads "N-bromo-N'-5,5-" and should read -- N-bromo-N'-chloro-5,5- --.

Signed and Sealed this

Twenty-first Day of November, 1989

Attest:

JEFFREY M. SAMUELS

Attesting Officer          Acting Commissioner of Patents and Trademarks